US011621060B1

(12) United States Patent
Mirza et al.

(10) Patent No.: US 11,621,060 B1
(45) Date of Patent: Apr. 4, 2023

(54) BIOMETRIC SAFE BLOOD DONOR CERTIFICATION AND GEO-LOCATION SYSTEM

(71) Applicant: PEER Technologies PLLC, Fairfax, VA (US)

(72) Inventors: Sohail K. Mirza, Fairfax, VA (US); Atiyya S. Mirza, Fairfax, VA (US)

(73) Assignee: PEER Technologies PLLC, Fairfax, VA (US)

( * ) Notice: Subject to any disclaimer, the term of this patent is extended or adjusted under 35 U.S.C. 154(b) by 0 days.

(21) Appl. No.: 16/669,424

(22) Filed: Oct. 30, 2019

Related U.S. Application Data

(60) Provisional application No. 62/752,429, filed on Oct. 30, 2018, provisional application No. 62/886,821, filed on Aug. 14, 2019.

(51) Int. Cl.
*G16H 10/40* (2018.01)
*G06Q 10/10* (2012.01)
(Continued)

(52) U.S. Cl.
CPC ............ *G16H 10/40* (2018.01); *A61B 5/1112* (2013.01); *A61B 5/1171* (2016.02);
(Continued)

(58) Field of Classification Search
CPC ............... G16H 10/40; H04W 12/033; G06K 9/00617; G06K 9/00288; G06K 9/00087;
(Continued)

(56) References Cited

U.S. PATENT DOCUMENTS 5,876,926 A * 3/1999 Beecham ............... G16B 50/40
435/5
6,808,503 B2 * 10/2004 Farrell ............... A61M 1/3675
210/252

(Continued)

FOREIGN PATENT DOCUMENTS

WO WO-2018022722 A1 * 2/2018 ............. G16H 10/40

OTHER PUBLICATIONS

Hamlin, Blood Donation and Life Saver-Blood Donation App, ICCICCT (Year: 2016).*

*Primary Examiner* — John B Strege
(74) *Attorney, Agent, or Firm* — Loginov & Associates, PLLC; William A. Loginov

(57) ABSTRACT

The system and method for biometric safe blood donor certification and geo-location system provides a safe blood donor biometric certification and geolocation tracking system that is an efficient, accurate, and portable device to acquire biometric data to authenticate identity of an individual and link the biometric identity to the blood test samples and results. This technology can unequivocally identify the person with their blood profile. The technology can track location of potential donor individuals with geo-location Global Positioning Satellite sensors and alert these individuals when a nearby patient requests their blood type. All eligible blood donors can be alerted about the opportunity to respond and accept the invitation for blood donation. Those who donate blood are removed from the eligibility list until they can safely donate again. This system eliminates the need for complex equipment and facilities to store donated blood for extended periods and eliminates waste of unused blood.

18 Claims, 5 Drawing Sheets

(51) Int. Cl.
*G06F 16/23* (2019.01)
*A61B 5/1171* (2016.01)
*A61B 5/1172* (2016.01)
*A61B 5/11* (2006.01)
*H04W 12/033* (2021.01)
*G06V 40/16* (2022.01)
*G06V 40/18* (2022.01)
*G06V 40/12* (2022.01)
*G01S 19/42* (2010.01)
*G06V 40/70* (2022.01)
*G06Q 10/105* (2023.01)

(52) U.S. Cl.
CPC .......... *A61B 5/1172* (2013.01); *A61B 5/1176* (2013.01); *G06F 16/2379* (2019.01); *G06Q 10/105* (2013.01); *G06V 40/1365* (2022.01); *G06V 40/172* (2022.01); *G06V 40/197* (2022.01); *H04W 12/033* (2021.01); *G01S 19/42* (2013.01); *G06V 40/70* (2022.01)

(58) Field of Classification Search
CPC .............. G06K 9/00892; G06Q 10/105; A61B 5/1171; A61B 5/1172; A61B 5/1176; A61B 5/1112; G06F 16/2379; G01S 19/42
See application file for complete search history.

(56) References Cited

U.S. PATENT DOCUMENTS

| | | | |
|---|---|---|---|
| 7,430,478 B2* | 9/2008 | Fletcher-Haynes .... | G16H 40/67 702/21 |
| 7,566,315 B2* | 7/2009 | Hirabuki .............. | A61M 1/3643 604/6.01 |
| 7,704,454 B1* | 4/2010 | Langley .............. | A61M 1/3656 422/44 |
| 9,697,337 B2* | 7/2017 | Goodnow, II ......... | A61B 5/155 |
| 2002/0013523 A1* | 1/2002 | Csore .................. | A61B 5/0002 600/368 |
| 2003/0004751 A1* | 1/2003 | Ng .................... | A61B 5/150809 705/2 |
| 2003/0154108 A1* | 8/2003 | Fletcher-Haynes .... | G16H 20/40 705/3 |
| 2007/0224985 A1* | 9/2007 | Choi .................... | G01C 21/20 455/433 |
| 2008/0208750 A1* | 8/2008 | Chen .................... | G06Q 10/087 705/50 |
| 2010/0049542 A1* | 2/2010 | Benjamin ............. | G16H 20/40 705/2 |
| 2012/0010553 A1* | 1/2012 | Alqvist ............... | A61M 1/0245 604/4.01 |
| 2016/0117492 A1* | 4/2016 | Chabanne ............. | G06F 21/32 726/19 |

* cited by examiner

BIOMETRIC SAFE BLOOD DONOR CERTIFICATION AND GEO-LOCATION SYSTEM

RELATED APPLICATIONS

This application claims the benefit of U.S. Provisional Application Ser. No. 62/752,429, filed Oct. 30, 2018, entitled BIOMETRIC SAFE BLOOD DONOR CERTIFICATION AND GEO-LOCATION SYSTEM, and U.S. Provisional Application Ser. No. 62/886,821, filed Aug. 14, 2019, entitled BIOMETRIC SAFE BLOOD DONOR CERTIFICATION AND GEO-LOCATION SYSTEM, the entire disclosure of each of which applications is herein incorporated by reference.

FIELD OF THE INVENTION

This invention relates to blood donation and donor management systems, and more particularly to identification, tracking, and notification of healthy donors with respect to recipients in need.

BACKGROUND OF THE INVENTION

Blood donation, storage, and distribution currently requires complex processes for identifying potential donors who are safe to donate blood, testing them for blood type and potential infectious agents and markers, and safely transporting and storing the donated blood until it is needed by a patient of that blood type. Some components of donated blood, such as clotting agents, decompose with time. Fresh blood is needed for some patients, making it difficult to urgently find the right blood donors.

Moreover, in certain regions, it is recognized that blood donation requires that a donor for a recipient in need be located in real time, as storage of fresh blood for one or more blood types may be highly limited, or totally unavailable. Such donors must also be reasonably healthy and capable of donating blood. Since the need for fresh blood may be critical on the part of the recipient, potentially meaning the difference between life and death, it is desirable to provide a mechanism that allows for ready identification and notification of willing donors with compatible blood type(s).

In a theater of war and/or conflict, injured personnel (e.g. warfighters, first responders, etc.) may require blood transfusions quickly, and a failure to provide a transfusion quickly can result in coagulopathy. Combat and/or disaster casualties requiring transfusion have high mortality, and whole blood transfusion offers significant survival benefit compared to component therapy. Whole blood is an FDA approved product when it is collected by a licensed blood donor center, tested for transfusion transmitted disease (TTD), and stored in CPD or CPDA1 anticoagulants. Whole blood can be stored for 21 days, but whole blood coagulation function decreases over time. Fresh whole blood (FWB, transfused within less than 5 days of collection) transfusion addresses all aspects of acute traumatic coagulopathy: tissue hypoperfusion, hemodilution, acidosis, hypothermia, inflammatory response, hyperfibrinolysis, endothelial dysfunction, dysfibrinogenemia, and platelet dysfunction. Furthermore, blood storage facilities can be difficult or impossible to maintain sufficiently close to potential injuries, including a theater of war.

Fresh donations are needed on the front lines for optimal resuscitation of actively bleeding personnel. Theater whole blood is superior to components, but optimal methods for managing donors, titers, Rh factor, and leukodepletion in transfusion of fresh whole blood remain unresolved. Furthermore, chaotic conditions under which FWB is required, such as active wartime or conflict, can increase the risk of clerical errors leading to major mismatch reactions.

SUMMARY OF THE INVENTION

This invention overcomes disadvantages of the prior art by providing a portable system that is an efficient and accurate device to identify and locate eligible safe blood donors. The system and method described herein is designed for users and workflows under chaotic conditions including active wartime, and can incorporate biometric identification of users/donors/recipients and can leverage bar code scanning to simplify documentation, so that a Walking Blood Bank can be created safely with a significantly decreased risk of error during chaotic situations.

The system and method described herein provides for improved speed and availability of fresh whole blood near inured individuals, including injured warfighters. Beneficially, fresh whole blood can provide red blood cells, platelets, and plasma in a physiologic ratio that can return to the bleeding patient what has been lost. Fresh whole blood has the right ratios of components, no degradation of platelet, clotting factor or RBC function, and is more readily available in austere conditions.

The device uses biometric data to unequivocally identify individuals during sampling and testing of their blood. The device and accompanying software stores blood test results for that person, including blood type and markers for hepatitis, HIV, and other infectious agents. The device and software track the individual's geolocation. When a patient or the patient's family or care giver requests that blood type, all nearby matching certified safe blood donors are alerted of the need for their blood type. The number of needed eligible blood donors who are first to accept the invitation are directed to go to the requested location for their blood type. The donors donate fresh blood. The donor is then removed from the eligible list until the required amount of time passes until they can safely donate again.

In an illustrative embodiment, a biometric identification system for use to accurately identify individuals can include an iris scan module for identifying an individual based upon their iris, a facial recognition module for identifying the individual based upon their face, and a finger print scan module for identifying the individual based upon their finger print, and a blood acquisition module for acquiring one or more blood samples from the identified individual. The biometric identity and blood sample linking system can include blood tests to identify blood type, check for infection markers, and certify the individual as a safe blood donor. The system can include geolocation of the individual using Global Positioning Satellites. Data related to the individuals can be communicated via at least one of a cellular telephone network and an encrypted satellite and/or terrestrial radio network. Personal identification data can be based upon a list of available individuals associated with an organization.

In an illustrative embodiment, a blood donation system can include a donor record database that can store donor records including blood type and donor identifying information, and at least two mobile devices. The mobile devices can include a donor data module storing donor records received from the donor record database, a location module that provides location information about donors and about the mobile device making a donation request, a matching module configured to match eligible donors to a recipient who has made a donation request, and a request module that requests identified donors to come to the location of the recipient to donate blood. The blood donation system can include a record updating module that updates donor records after a donation.

In an illustrative embodiment, a method for donating fresh whole blood can include requesting a blood donation, confirming the identity of the requester, referring to a donor database to determine the requester's blood type, matching the requestor to eligible donors who are in the donor database and have a compatible blood type for donating to the requestor, and sending a request to one or more eligible donors to donate blood. The method can include providing a location of the requestor. Matching the requestor to eligible donors can include matching eligible donors who are closest to the requestor. Sending a request to one or more eligible donors to donate blood can include sending a request to one or more eligible donors to donate blood at the requestor's location. The method can include updating the donor database to indicate when the one or more donors donated blood and who received the blood. The method can include updating the donor database in indicate when the recipient received blood and whose blood the recipient received. Confirming the identity of the requester can include confirming the identity of the requester using biometric data. The method can include confirming an identity of the one or more donors using biometric data before donation.

BRIEF DESCRIPTION OF THE DRAWINGS

The invention description below refers to the accompanying drawings, of which.

DETAILED DESCRIPTION

I. System Overview and Usage

Figure 1:
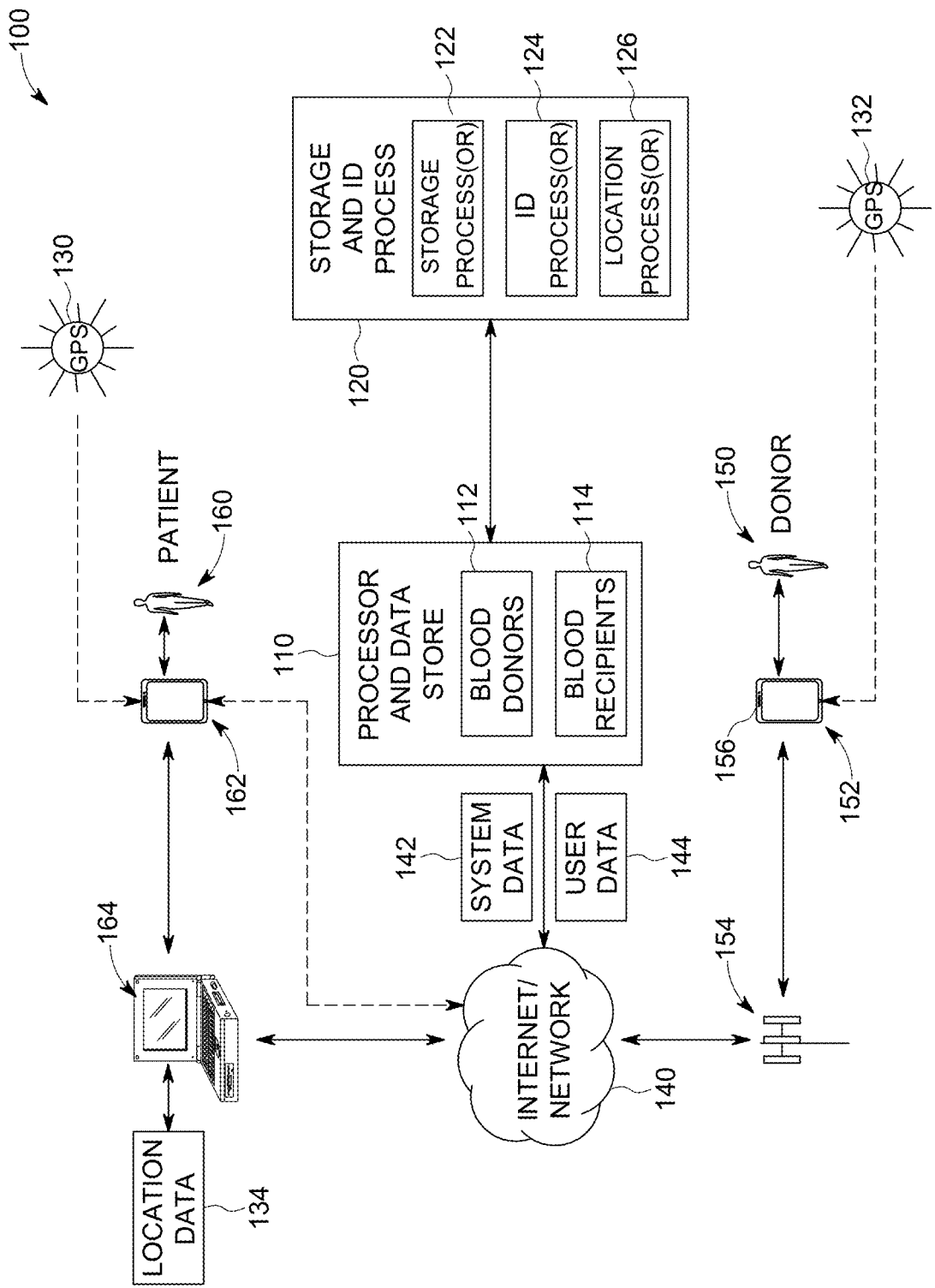
FIG. 1 is a diagram of a system for identifying and locating compatible blood donors based upon stored information and biometric information using a handheld device, according to an illustrative embodiment.

FIG. 1 is a diagram showing an overall system arrangement 100 for a blood donation identification, location and notification system according to an embodiment. The system includes a central computing device—for example a cloud-based server 110 that stores relevant information on participating blood donors 112 and recipients 114. This information can be arranged in any acceptable form, such as a database. The information is handled by a process(or) 120 instantiated on the server 110 or remote therefrom—for example distributed onto local computers or other computing devices (e.g. PCs, laptops, tablets and handheld cell phones). The process(or) 120 includes a plurality of functional processes/ors or modules, including, but not limited to a storage process(or) 122 that accesses and stores information 112, 114; an identification (ID) process(or) 124 that handles stored and input identification data from various sources (e.g. biometric data, logins, etc.) and validates access to the system, and a location process(or) 126 that determines locations of donors and recipients based upon real time geolocation position (e.g. via GPS satellites 130, 132) and/or fixed location data 134, such as an address residing on a facility computer or user-input location. The location process(or) 126 determines proximity based upon various metrics (which can include maximum distance, similar geographic area—the same city, town, province, etc., and/or other metrics that can be established by the system or via user preferences). System-generated data 142 can be transmitted from the server to users via a network 140, such as the public Internet, private network, a closed-circuit network, peer-to-peer communication, radio communications, or other means for the transmittal of information. User-input data 144 can be delivered to the server 110 via this network 140 that can include public internet, private network, a closed-circuit network, peer-to-peer communication, radio communications, or other means for the transmittal of information.

Users of the system can include clinicians, prospective donors and/or patients/recipients. The donors 150 can be in communication with the system via an appropriate device 152—for example, a laptop computer, a handheld device such as a two-way radio, a tablet, or smartphone that can allow for geo-location via (e.g.) GPS satellites 132 and/or cell antenna (154) triangulation and location reporting. The donor's device 152 can include an application that communicates with the server 110 using known protocols and techniques. The application either selectively (when requested by the server) or continuously reports the donor's location to the server. The donor can have already preloaded biometric information—for example an iris or fingerprint scan using the device camera 156, or an appropriate mechanism (e.g. a fingerprint reader on another user device—such as a laptop). This is part of the stored donor information 112. Alternatively, all storage of vital information can remain on the device 152, and a basic ID code can be transmitted to and from the server to identify the donor. SMS or another protocol can be used to transmit such data. The donor 150 can have been screened by a clinician or other individual for blood type and health status and this information can be stored either in the server 110 or the device 152. The server 110 or device 152 can also log the last time the donor 150 gave blood so that he/she is prevented from over-donating or requires a new screening to verify that his/her blood is still healthy.

The patient/recipient 160 is shown in a clinical setting and is being scanned by a device 162 in accordance with an embodiment. The device 162 can be directly linked to the Internet 140 via a cellular connection or other network connection, or can be connected directly or indirectly to a clinical computing device 164 and/or the clinic data network. In one form, the device 162 is a smartphone with an application loaded on it adapted to connect to the server. The device can locate the patient based upon (e.g.) GPS satellite 130 information, and/or another mechanism, including prestored location data 134 associated with the clinical computing device 164, or input by the user or another person into the device 162.

More generally the system 100 and/or associated device 162 uses biometric data to unequivocally identify individuals (donors) during sampling and testing of their blood. The device and accompanying software stores blood test results for that person, including blood type and can include markers for hepatitis, HIV, and other infectious agents. Potential donors can complete a donor questionnaire and/or physical examination prior to becoming eligible donors. The donor questionnaire and/or physical examination can include blood test results for blood type, antigens, and markers for hepatitis, HIV, and other infectious agents as required by the FDA. The system 100 can capture and save the donor information from the donor questionnaire and/or physical as part of the donor data. The system 100 can also track the results of testing over time, and can update donor data in the database as test results change. The app can track clinicians, donors, recipients, date/time/location stamps, and can automatically update the database and notify appropriate individuals of new test results.

The system 100 can leverage biometric identification methods to prevent hemolytic reactions from blood type mismatch. One important safety consideration in FWB transfusion is acute hemolytic transfusion reaction due mismatch between the ABO blood type of the donor and recipient (major mismatch). To avoid this risk, the system 100 can use biometrics to eliminate risk of hemolysis. Since blood type on identification tags is occasionally incorrect and cannot be relied upon to determine blood type for either donors or recipients, the system 100 can use one or more of finger print, iris, and/or facial recognition to verify identity of donors, recipients, clinicians and/or other users of the system 100. The system 100 can automate processes for blood donation and a walking blood bank, including the use of biometric data, to reduce the risk of life threatening errors and mismatches when attempting to match donors to recipients in chaotic circumstances including tactical fire and mass casualty scenarios. The system 100 provides easy to use and fail safe methods to implement blood donations including walking blood banks, and can make documentation and record keeping/updating easier under austere or chaotic conditions than previous systems. The system can provide for hands-free data entry methods, including voice capture, for data entry in a chaotic or tactical setting, including a point of injury, providing care enroute, or other places where conventional data entry can be difficult. Hands free data entry can include donation requests, record updates, and/or other human interactions with the system.

The system 100 can perform donor management to coordinate recipients with donors in real time. In various embodiments, the system 100 can also manage inventories of blood donations that have been previously donated, including updating records with new blood products as they are received into inventory. By way of non-liming example, the system can keep track of each unit of donated blood, including data such as the identity of the blood donor, donor data such as blood type, etc., and the location of the unit of blood, and can coordinate recipients with previously-donated blood units, similar to coordination of recipients with fresh blood donors. The system can monitor the status of blood dispensation and update records accordingly.

Figure 2:
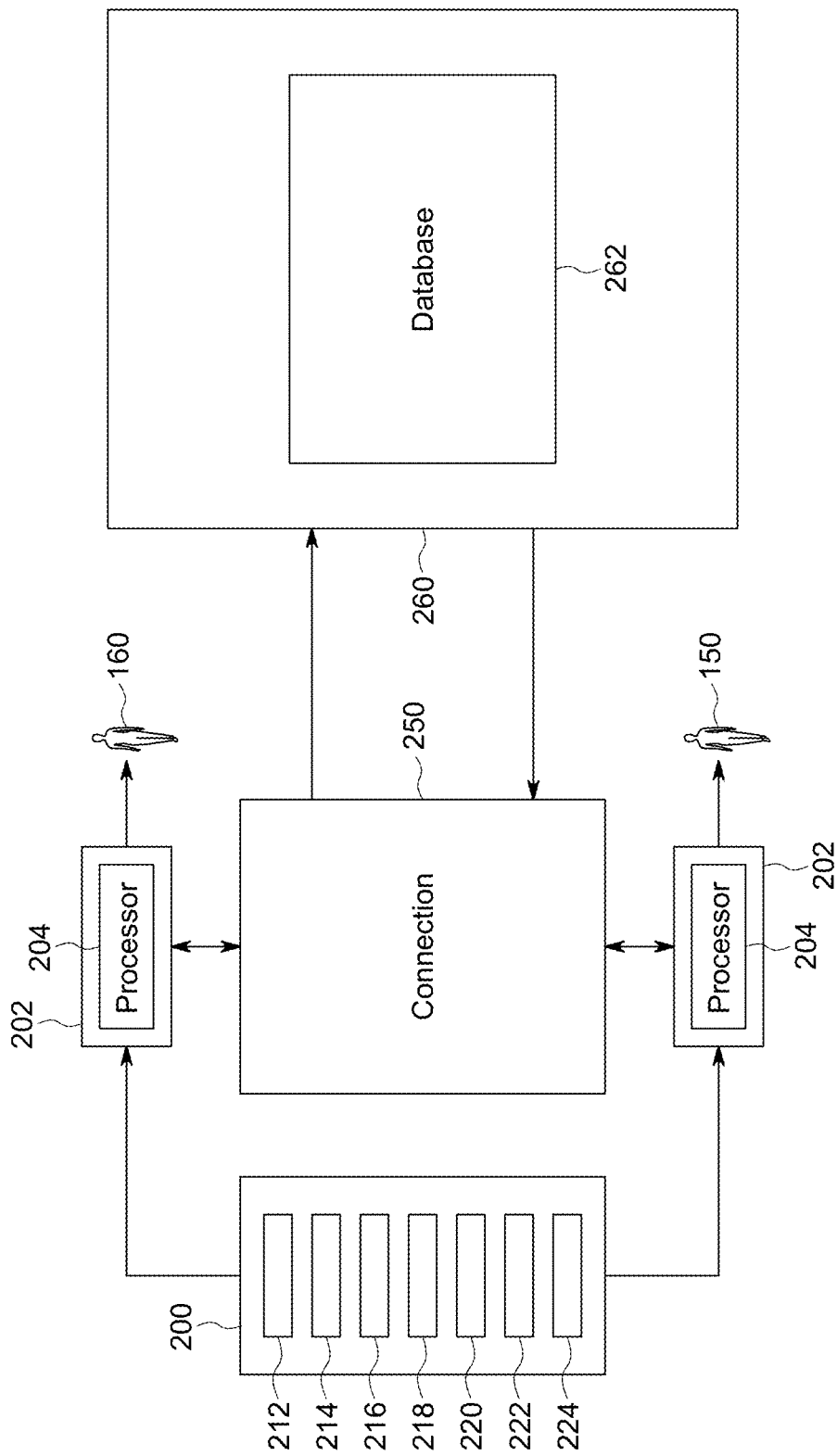
FIG. 2 is a diagram of an exemplary mobile technology that can provide blood donor biometric certification and geolocation tracking under reduced connectivity, according to an illustrative embodiment.

FIG. 2 is a diagram of an exemplary mobile technology that can provide blood donor biometric certification and geolocation tracking under reduced connectivity, according to an illustrative embodiment. In various embodiments, the mobile technology 200 for providing blood donor biometric certification and geolocation tracking can be configured as an executable application (e.g., an "app") for a cell phone, such as an iOS or Android app, or can be an app for a mobile computing device such as a tablet, or can be incorporated into a purpose-built device, or other configurations. When the mobile technology is described herein for simplicity as a phone app, it should be clear that various other embodiments of the technology are also specifically contemplated.

A blood donation recipient 160 can have a device 202 with the app 200 installed on the device 202. Blood donation recipient 160 can be a person in need of blood, or can be a caregiver associated with the person in need of blood. A blood donor 150 can also have a device with the mobile app 200 installed on the device. Blood donor 150 can be a person who is able to give blood, or another person associated with the blood donor who can assist or coordinate the blood donation. The app 200 can run on the processor 204 of the device 202. The app 200 have a donor data module 212, a recipient data module 214, a matching module 216, a biometric data module 218, a location data module 220, a request module 222, and a records update module 224.

The donor data module 212 can maintain donor data for all individuals who are participants in the system and can potentially be donors 150. The recipient data module 214 can have the recipient data for a recipient 160 who is requesting a blood donation. The matching module 216 can identify donors from the list of potential donors using information such as blood type and physical location to identify one or more donors 150 to donate blood to the recipient 160. The location data module 220 can maintain information about the locations of potential donors. Under low-connectivity or no connectivity conditions, the location data module 220 can maintain the most recently available location data for each available donor, and the location data module can update the location data whenever updated data is available. The location module can also provide the location of the recipient when a request is made for a donation. The biometric data module 218 can collect biometric data, and can compare the data to the donor data records to guarantee a positive identification for potential recipients and for potential donors. The biometric data can be acquired initially when a potential donor is first enrolled in the system, and the biometric data can be stored with other donor data. The biometric data module can then compare biometric data collected at the time of the donation or donation request with biometric data collected previously and stored with the donor data. The request module 222 can request that the identified donors arrive at the recipient's location to donate blood to the recipient. The records update module 224 can update records after a donor donates blood and/or a recipient receives blood. The records update module 224 can update the donor's records to indicate the donation, the recipient records can be updated to indicate the blood received, and/or inventory records can be updated to indicate that blood was dispersed. The record updating function is explained in more detail further below.

The app 200 can allow a recipient 160 to make a request for a blood donation over a secure connection 250. The app can use the donor database to identify nearby potential donors, and request a donation from identified donors. The app can send the request over the connection 250 to the devices associated with the identified requested donors 150. The app can then trigger a message on the device 202 of the donor 150, indicating a request for a blood donation from the donor 150. Connection 250 can be a secure connection that can include tactical radio, cell towers, phone-to-phone connections, or other forms of connections including data connections. The app 200 can also provide location data from each device over the connection 250, so that the location of each device is known by the system.

The system can include a clinical computing system 260. Clinical computing system 260 can include a theater medical data store database 262. The theater medical data store database 262 can store donor data, recipient data, and location and proximity data. The clinical computing system 260 can maintain and coordinate data between the apps 200 on each device 202 and the theater medical data store database 262. The clinical computing system can update the data on each device 202 whenever connectivity is available, and the app 200 can operate on each device 202 using the data stored on that device 202 when connectivity is low or unavailable. The app can update the data stored on a device 202, including donor data such as the date and time of a donor's most recent donation, and the app can update the database 262 with the new donor data when connectivity is available. In various embodiments, devices 202 can be connected to the clinical computing system 260 to exchange data between the device 202 and the database 262 using various wired or wireless connections. When connected, the device 202 and the clinical computing system 260 can both provide data updates to the other. In various embodiments, two or more devices 202 can exchange data directly between the devices over the connection 250. Data transfer can be compressed to minimize data transfer needs, if necessary under low connectivity conditions.

The system can allow users working in disconnected, intermittent, and low-bandwidth connectivity environments to continue to perform local business processes and functions required to ensure the integrity of the supply chain management and quality of blood products while disconnected from the network. This can include being able to view, modify, and update blood donor availability, previously donated blood product inventories, update test results, identify previously-screened donors with documented recent Transfusion Transmitted Disease (TTD) testing results, and notify eligible safe donors to report to the location where their blood type is needed. Biometric technology can unequivocally identify the person with their blood profile based on stored information. Stored data from various location methods (Geo-location through Global Positioning Satellite sensors in the Continental United States (CONUS) and other secure location methods OCONUS) can be used to identify and alert eligible blood donors when a nearby patient requests their blood type. Location information can include real time geolocation position (e.g. via GPS satellites, tactical radio, other secure localization process), and/or fixed location data, such as positions of a particular squad or military unit that can be acquired from geolocation or from deployment information. The location data for a potential recipient 160 and/or potential donor 150 can be determined from any of the above methods, or can be entered into a device 202 manually. Eligible donors can be determined from donor data including blood type, and location information. Various metrics can be used in determining the suitability of individuals in different locations, including maximum distance, similar geographic area, or other metrics. All eligible blood donors can be alerted using secure communication channels available to field personnel, until the needed number of blood donors have accepted the invitation for blood donation. Those who donate blood will be removed from the eligibility list until they can safely donate again. This system will reduce the need for complex equipment and facilities to store donated blood for extended periods and waste of unused blood.

A mobile app 200 can enable a smartphone or other mobile device to function as an efficient, accurate, and portable device that can acquire biometric data to authenticate identity of an individual, and can link the biometric identity to the donor history questionnaire, blood test results, blood samples, and/or donated blood products. The technology can establish a "Walking Blood Bank" for transfusion of fresh whole blood under austere conditions, such as, for example, the conditions specified in the Joint Trauma System Clinical Practice Guideline Whole Blood Transfusion (CPG ID:21). The app can use biometric methods such as, for example, iris scan, fingerprint scan, facial scan, etc. to verify the identity of donors and/or recipients.

The mobile app 200 can identify, locate, and track healthy potential donors, and the mobile app can use various communication methods, including secure communication methods, cellular communication, radio communication, internet, etc. to identify and alert nearby eligible donors when there is emergent need to transfuse blood. The mobile app 200 can be used to find a donor for a patient in need of type-specific fresh whole blood. The system can be used to locate individuals nearby the location where that individual's blood type is needed. When a blood recipient 220, such as patient or squad member or care giver requests, that blood type, nearby matching certified safe blood donors 150 can be alerted of the need for their blood type. The number of needed eligible blood donors who are first to accept the invitation will be directed to go to the requested location for their blood type, so that the donors 150 can donate fresh whole blood to a blood donation recipient 220 in need. After a recipient receives blood, the recipient records can be updated on a device to indicate what blood was received, how much was received, when it was received, and from which donor(s), and can be updated on the database when connectivity allows. After a donor donates blood, the donor records can be updated on a device, and can be updated on the database when connectivity allows. The donor 150 can then be removed from the eligible donor list until the individual is eligible to donate again. The donor record updates can include who received the donor's blood and when the donor donated. The mobile app 200 can facilitate the process for updating donor screening, collecting fresh whole blood, and labeling/testing/transporting the donation according various standards, including FDA standards for licensed blood manufacturing facilities.

Figure 3A:
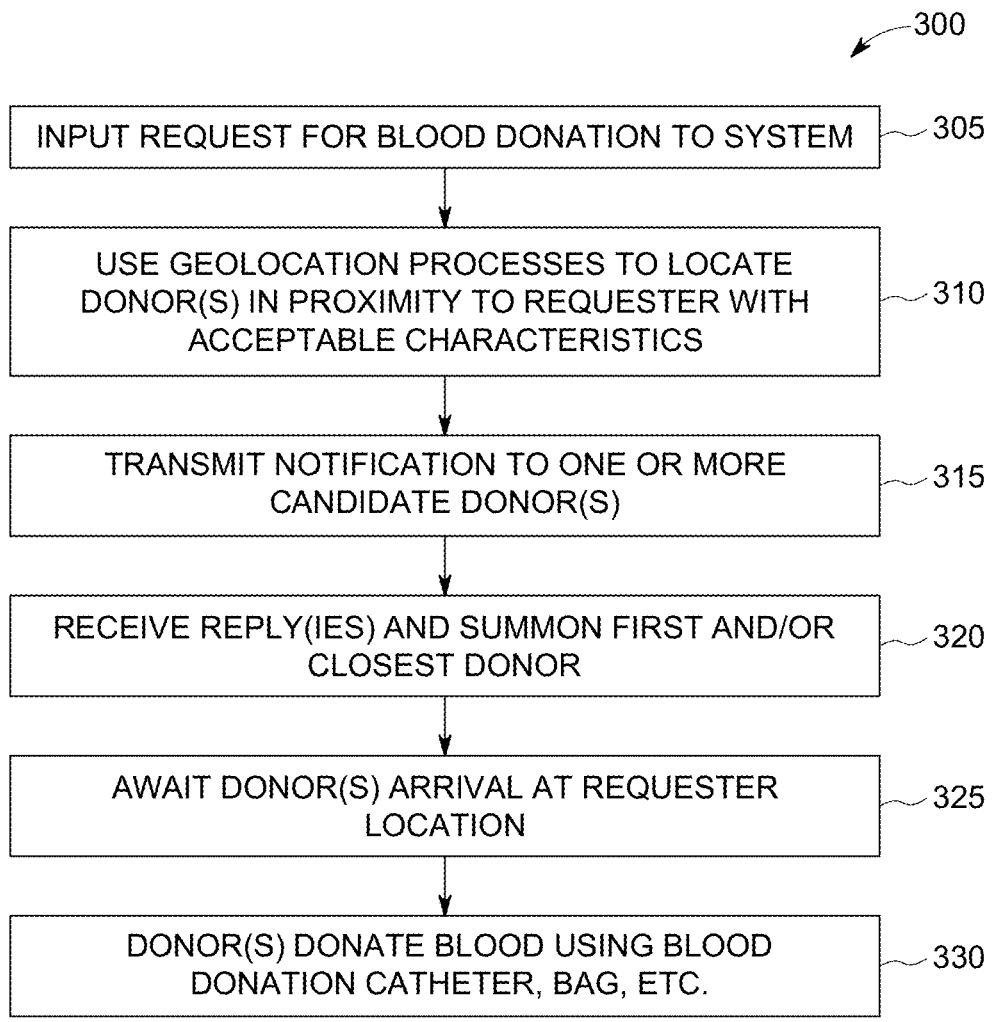
FIG. 3A is a flow diagram showing a procedure performed with respect to a donor smartphone or other communication device to locate, identify and notify donors of a need for blood by a recipient using the system of FIG. 1, according to an illustrative embodiment.

FIG. 3A shows a procedure 300 for requesting a blood donation using the system of FIG. 1. At 305, the clinician or recipient device uses an application, web address, or other means for transmittal of information to place a request for blood donation in the name of the recipient. The request can be initiated by the blood recipient, or a caregiver or related individual. Placing a request for a blood donation for a recipient can include the use of biometric data to positively identify the recipient. By way of non-limiting example, using biometric data to positively identify the recipient can include a fingerprint or iris scan of the patient. This can enable positive identification even when a recipient is unconscious or incoherent. The recipient is confirmed in the list of members via the database. Confirmation of the recipient in the database also results in confirmation of the requested blood type, because the blood type of the recipient is stored in the donor database. Note that donors and recipients can be part of the same "pool" within the system as members—that is, any member can be a donor or a recipient, with donors verified as healthy. In this manner, should an otherwise healthy member have an accident, other donors are available to help that recipient member who, in turn, donates when able to do so. At 310, the device and software can track the donor individual's geolocation. Tracking the location of potential donors can include the use of secure localization technologies used on front lines. The geolocation of all tracked donors can be compared to the location of the requester (which can be determined by fixed coordinate data or via another GPS geolocation activity). At 315, when a patient or the patient's family or care giver requests that blood type, nearby matching certified safe blood donors, who are members in the database, are alerted/notified of the need for their blood type. In various embodiments, the notification of nearby donors can take place immediately and automatically after the recipient is positively identified at 305.

In various embodiments, the system can operate under low-connectivity conditions, in which case the system can use any available means, such as two-way radio, to notify all potential donors. A message to a potential donor can take the form of a text-to-speech message sent over a tactical radio or other secure communication channels available in the field. Under low-connectivity conditions, potential donors can be some or all people who are listed in a database of possible donors that can be stored in the app or on the device. Under low-connectivity conditions, the locations for potential donors can be assumed to be the potential donor's last recorded location, which can be stored in the database with other information about the potential donors. The database of available donors can be updated from the theater medical data store whenever connectivity is available.

At 320, the number of needed eligible blood donors who are first to accept the invitation are directed to go to the requested location for their blood type. This can include accepting the invitation via the donor's smartphone using (e.g.) the application thereon, a web portal associated with the system and method, communication over two-way radio, an SMS text message to the service or an address of the request, or other means of communication or transfer of information.

At 325, the donors arrive at the requested location. When eligible donors arrive, medical staff can identify the potential donors by scanning an ID such as a Controlled Access Card, and/or through collection of biometric data, such as finger print, iris or facial scan to verify identity. Confirmation of the donor in the database also results in confirmation of the donor's blood type, because the blood type of the donor is stored in the database. After the blood type of the recipient and of the donor have been confirmed, the match between recipient and donor can be automatically confirmed by the system, thereby reducing errors that can occur in chaotic situations such as wartime. The system can display a message such as "safe to donate" to indicate that the match has been confirmed. After donor eligibility is confirmed, the app can trigger printing of labels. In various embodiments, the app can also facilitate administration of the Donor History Questionnaire to update each donor's eligibility.

At 330, the donor can donate fresh blood. After the system displays a "safe to donate" message, a clinician can proceed with the blood donation. Donating fresh blood can include using conventional catheters, storage bags and other associated equipment. Blood can be delivered directly to the recipient or stored for further use—including separation of components as appropriate. The system can allow a clinician to indicate in the system that blood has been dispensed to a recipient by scanning a barcode or other label, and making a quick swipe or click to indicate that the blood was delivered to the recipient. The inventory records and/or the recipient's records can be updated automatically to reflect that the labeled unit of blood was dispensed to the recipient.

Figure 3B:
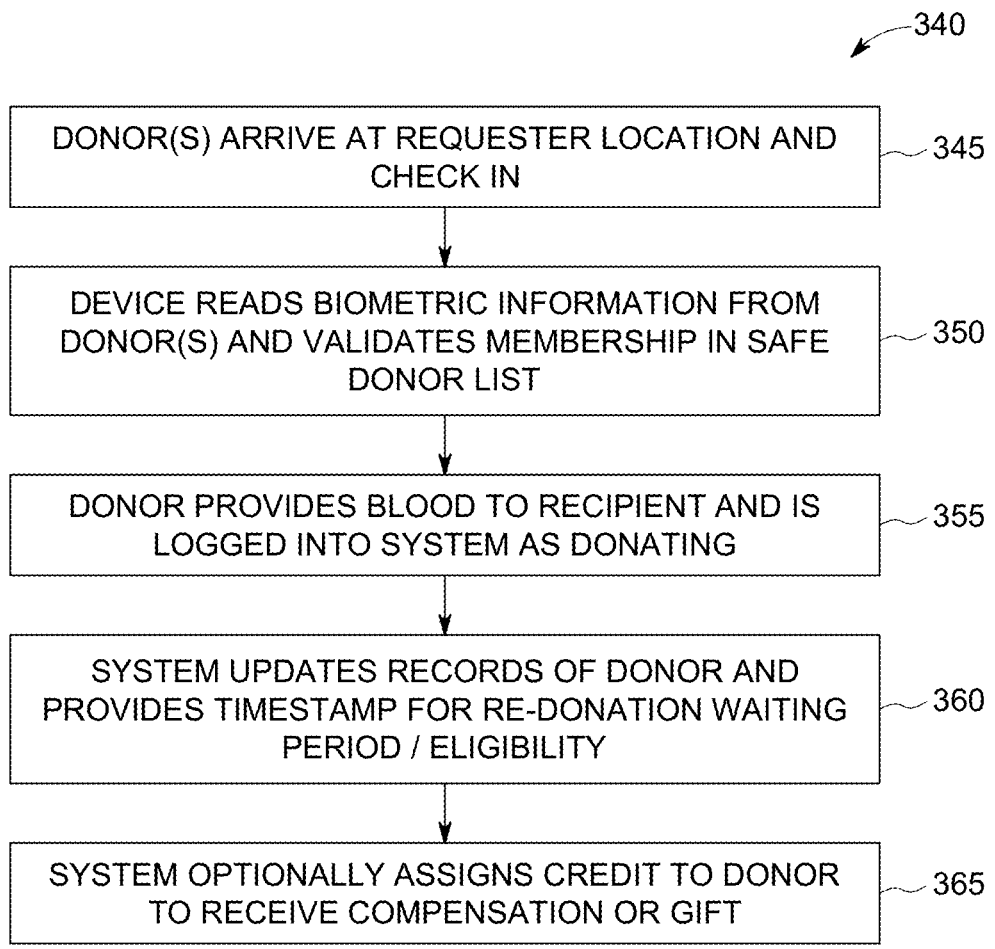
FIG. 3B is a flow diagram showing a procedure performed with respect to a recipient in need of blood using a device associated with a clinic or other caregiver, or the recipient him/herself in notifying proximate donor candidates and verifying the identity of such using biometric information, according to an illustrative embodiment.

Referring to the procedure 340 in FIG. 3B, a partially overlapping set of steps is performed using the requester device, which can be a dedicated device used by the clinic—for example, a smartphone, laptop, tablet or PC, or can be a smartphone used generally by a clinician or even the recipient. In general, the device can be arranged with an appropriate application or web portal to perform the recipient side of the overall system and method herein. At 345 of the procedure 340, after a recipient places a request using a device, the donor arrives at the recipient location and checks in. At 350, the device reads the donor's biometric information—for example a facial scan, iris scan and/or fingerprint scan, and validates that the donor is on the safe list for donation via the server database 112 or other stored information (for example a list stored on the recipient's smartphone or local clinic's device directly). Then, once verified, at 355 the donor provides blood using conventional equipment as described above. Once the donation is complete, or after another "handshake" is made with the system, at 360 the donor is then removed from the eligible list until the required amount of time passes until he/she can safely donate again. The system can update the donor records to include the date and time of the most recent donation, and a time for donation re-eligibility. The system can update the donor information on the device, and the updated donor data can also be updated in the server database 112 at the time of donation, or when connectivity to the server database is available. All data can be encrypted by the system at rest and in transit. End to end encryption of data in transit can unsure that the data is not tampered, and if the data appears to be tampered, the encryption algorithms can ensure that the data is discarded.

At 365 of the procedure 340 the system can optionally assign a credit to the donor for their service/assistance. This can be in the form of (e.g.) monetary compensation, gift cards, coupons for discounted purchases, prizes, or a general suggestion that the recipient and/or family members provide an appropriate gift to the donor to recognize his/her service.

Note also that the system application used by donors or recipients can include a data-filtering process where it is desired to limit the prospective group of related parties in a blood-donation event to family members, friends, neighbors, individuals in the same platoon or other military group, etc.

II. Exemplary Device

Figure 4:
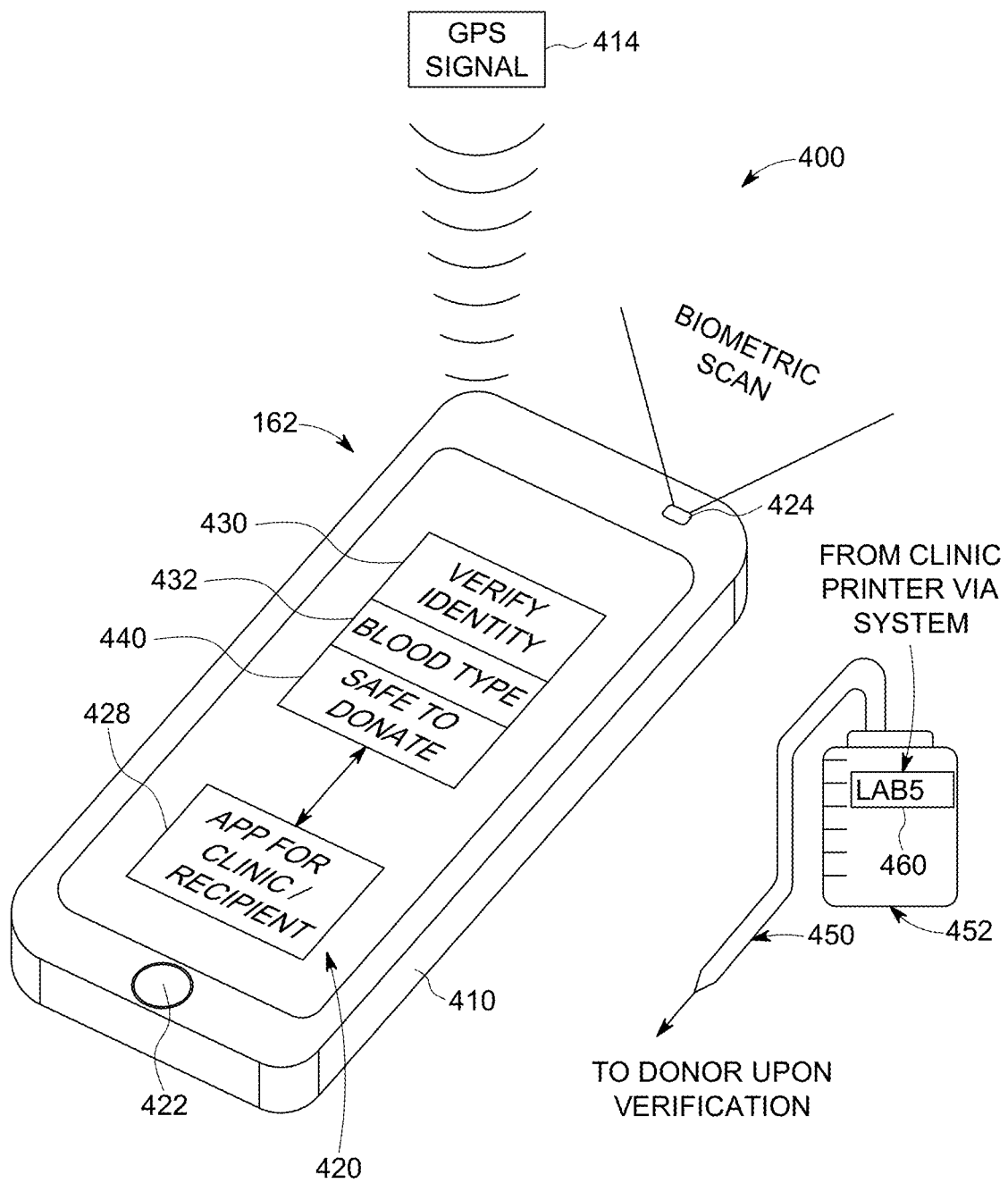
FIG. 4 is a diagram showing a biometric identification and blood sampling device for use with the system and method herein, according to an illustrative embodiment.

Referring to FIG. 4, an arrangement 400 including an exemplary requester device 162 is shown. In this example it takes the form of a smartphone that is either of general use or purpose-dedicated. In alternate embodiments, as described above, other devices—including a purpose-built device—can be substituted. The device 162 includes a housing 410 with a touchscreen 420 or other appropriate (e.g. graphical) user interface, as well as other appropriate function buttons 422. As described above, the device can communicate with GPS satellites and associated signal 414 to determine geolocation. This can be attained by other known mechanisms as described above (e.g. input coordinates/address, IP address, cell tower location, etc.). In addition to an operating system and various conventional applications, the device 162 is also loaded with the system application 428. This application 428 includes or integrates with other applications using (e.g.) appropriate APIs—such applications including conventional and/or customized verification and scanning applications, web browsers, text messengers, etc. The housing includes at least one camera/scanning device 424 and appropriate application for handling acquired image data. In this embodiment, the scanning device 424 is adapted to acquire biometric (image) data, and process such data to ensure the identity of the scanned individual (application display 430). The donor's statistics (name, age, blood type (display 432), health conditions, etc.) can be listed as well. Notably, the application 428 displays a "safe to donate" indicator 440 in this example. This allows the clinician to proceed with blood donation using a conventional catheter 450, storage bag 452, etc. as shown.

Note that while scanning of donors is described above, the device 162 can also scan and confirm the identity of the recipient and confirm that individual's vital statistics (name, age, blood type (display 432), health conditions, etc.) as a member of the system. This can be particular helpful if the recipient is unconscious or incoherent.

Note that the device can communicate with clinic computing systems that produce/print (e.g. self-adhesive) labels according to conventional printing techniques. Such labels 460 can be printed and applied to blood storage bags, charts, etc. indicating the donor and/or recipient's information.

III. Further Applications

It is expressly contemplated that the system provided herein can be applied to a variety of environments and circumstances in which safe blood donation is required. In various embodiments, the system and method provided herein can be applied to institutional environments with large groups of people, including institutions with hundreds, thousands, or more individuals that may have a need for blood donors. Such an organization can be a military unit, non-governmental organization (NGO), multinational corporation, etc. In an embodiment, the organization is part of the defense establishment and is typically deployed in a theatre of operations. In this embodiment, the communication can be provided by encrypted (digital) radio communications (e.g. field radios and satellite units), which can be substituted functionally for the above-described cellular communication. Likewise, various civilian and/or military geolocation systems can be employed. These can include terrestrial radio/EM-based location systems and/or satellite based systems.

As used herein, therefore, the terms cell or cellular and GPS should be taken broadly to include other communication and location modalities capable of carrying out similar data transfer and position finding functions.

IV. Conclusion

It should be clear that the above-described system and method provides an effective solution to providing safe, fresh blood to recipients in need where supplies of readily stored blood are not available. This system and method can be applied to a wide group of individuals, or to a more limited group—for example those with rare blood types (such as AB negative) that, even in advanced regions, may be lacking in sufficient blood supplies. Overall, this system and method enhances the security of patients in ensuring that fresh blood will be provided. Also notably, this system and method can increase community involvement in the care and treatment of those in need. In further embodiments, this system and method can be expanded to other modalities of communication and employed in more closed personnel-organizational systems such as corporations, the military, governmental agencies (e.g. law enforcement, first responders, etc.), NGOS, etc.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, while biometric information is used to verify donors (and potentially recipients) it is contemplated that other unique information, such as a scanned ID card, data (e.g. RFID) chip, input PIN/passcode, etc., can be used for validation. Also, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A biometric identification system for use to accurately identify individuals, comprising:
    a donor computing device, comprising:
        a geolocation module for determining a geolocation of the donor computing device;
        a donor iris scan module for identifying a donor based upon a donor iris;
        a donor facial recognition module for identifying the donor based upon a donor face; and
        a finger print scan module for identifying the donor based upon a donor finger print;
    a recipient computing device, comprising:
        a geolocation module for determining a geolocation of the recipient computing device;
        a recipient iris scan module for identifying a recipient based upon a recipient iris;
        a recipient facial recognition module for identifying the recipient based upon a recipient face; and a recipient finger print scan module for identifying the recipient based upon a recipient finger print;
one or more cloud-based servers configured to:
store a list of recipients in a recipient database, wherein the recipient is one recipient of the list of recipients, each recipient of the list of recipients is associated with a recipient blood type by the recipient database, and each recipient of the list of recipients is associated with a recipient record;
store a list of donors in a donor database, wherein the donor is one donor of the list of donors, each donor of the list of donors is associated with a donor blood type by the donor database, and each donor of the list of donors is associated with a donor record;
identify the recipient based upon at least one of the recipient iris, the recipient face, or the recipient finger print;
transmit a request for blood to the donor computing device based upon the geolocation of the donor computing device, the geolocation of the recipient computing device, a blood type associated with the recipient by the recipient database, a blood type associated with the donor by the donor database, a recipient record associated with the recipient, and a donor record associated with the donor;
identify the donor based upon at least one of the donor iris, the donor face, or the donor finger print;
transmit the geolocation of the recipient computing device to the donor computing device, wherein the donor computing device is further configured to display the geolocation of the recipient computing device;
receive a donor confirmation from the donor computing device; and
transmit the geolocation of the donor computing device to the recipient computing device, wherein the recipient computing device is further configured to display the geolocation of the donor computing device;
an identification device at the geolocation of the recipient computing device, wherein the identification device is configured to:
identify the donor based upon at least one of the donor iris, the donor face, the donor finger print, or by scanning a form of identification;
identify the blood type associated with the donor by the donor database of the one or more cloud-based servers;
identify the blood type associated with the recipient by the recipient database of the one or more cloud-based servers; and
confirm that the blood type associated with the donor and the blood type associated with the recipient are a match; and
a blood acquisition device for acquiring a first volume of blood from the donor and delivering a second volume of blood to the recipient wherein the first and second volumes of blood comprise the same blood and may be the same volume, and wherein the blood acquisition module is further configured to:
transmit a donation confirmation to the one or more cloud-based servers, wherein the donation confirmation comprises information indicating the first volume of blood acquired from the donor, a first time when the first volume of blood was acquired, the second volume of blood delivered to the recipient, and a second time when the second volume of blood was delivered to the recipient,
wherein the one or more cloud-based servers are further configured to:
update the donor record associated with the donor to comprise the information indicating the first volume of blood and the first time when the first volume of blood was acquired from the donor;
update the recipient record associated with the recipient to comprise the information indicating the second volume of blood and the second time when the second volume of blood was delivered to the recipient;
transmit the information indicating the first volume of blood and the first time when the first volume of blood was acquired from the donor to the donor computing device;
transmit the information indicating the second volume of blood and the second time when the second volume of blood was delivered to the recipient to the recipient computing device.

2. The biometric identification system as set forth in claim 1 wherein the donor computing device further comprises a blood scan module for performing blood tests to identify blood type, check for infection markers, and certify the individual as a safe blood donor.

3. The biometric identification system as set forth in claim 2 wherein geolocation of the donor computing device is tracked using Global Positioning Satellites.

4. The biometric identification system as set forth in claim 1 wherein data related to at least one of the donor or the recipient is communicated via at least one of a cellular telephone network, an encrypted satellite, and/or a terrestrial radio network.

5. The biometric identification system as set forth in claim 4 wherein the data related to the donor is based upon a list of available individuals associated with an organization.

6. The biometric identification system as set forth in claim 1 wherein, when the donor computing device is in a low-connectivity condition, the geolocation comprises a last recorded location stored in a location data module of the one or more servers.

7. The biometric identification system as set forth in claim 1 wherein
the donor computing device comprises a donor mobile phone; and
the recipient computing device comprises a recipient mobile phone.

8. The biometric identification system as set forth in claim 1 wherein the identification device and the recipient computing device comprise a single device.

9. The biometric identification system as set forth in claim 1 wherein the identification device, the blood acquisition device, the donor computing device, and the recipient computing device comprise different physical devices.

10. The biometric identification system as set forth in claim 1 wherein the identification device and the blood acquisition device comprise a single device.

11. The biometric identification system as set forth in claim 10 wherein the identification device is further configured to identify the recipient based upon at least one of the recipient iris, the recipient face, the recipient finger print, or by scanning a form of identification.

12. The biometric identification system as set forth in claim 1 wherein the one or more cloud-based servers are further configured to remove the donor from the donor database in response to the information indicating the first volume of blood and the first time when the first volume of blood was acquired from the donor.

13. The biometric identification system as set forth in claim 1 wherein the recipient database and the donor database are the same database.

14. The biometric identification system as set forth in claim 13 wherein the list of recipients and the list of donors are the same list.

15. The biometric identification system as set forth in claim 1 wherein the donor record further comprises information indicating a credit to the donor, and wherein the one or more cloud-based servers are further configured to update the donor record associated with the donor to add the credit in response to the donation confirmation.

16. The biometric identification system as set forth in claim 15 wherein the credit comprises one or more of monetary compensation, a gift card, a coupon, or a prize.

17. A biometric identification process for accurately identifying individuals in a blood donation transaction, the biometric identification process comprising:
    storing a list of recipients in a recipient database on one or more cloud-based servers, wherein each recipient of the list of recipients is associated with a recipient blood type and a recipient record by the recipient database;
    storing a list of donors in a donor database on the one or more cloud-based servers, wherein each donor of the list of donors is associated with a donor blood type and a donor record by the donor database;
    determining a recipient geolocation of a recipient computing device;
    determining an identity of a recipient of the list of recipients by a recipient biometric identification process comprising at least one of:
        scanning an iris of the recipient with the recipient computing device to determine recipient biometric iris information and identifying the recipient based on the recipient biometric iris information,
        scanning a face of the recipient with the recipient computing device to determine recipient biometric facial information and identifying the recipient based on the recipient biometric facial information, or
        scanning a finger print of the recipient with the recipient computing device to determine recipient biometric finger print information and identifying the recipient based on the recipient biometric finger print information;
    receiving, at the cloud-based servers:
        a request for blood from the recipient computing device,
        the recipient geolocation of the recipient computing device, and
        the identity of the recipient;
    determining a recipient blood type associated with the identity of the recipient according to the recipient database;
    determining an identity of a donor of the list of donors, wherein a donor blood type associated with the identity of the donor according to the donor database is a blood type capable of being donated to the recipient based on the recipient blood type associated with the identity of the recipient according to the recipient database;
    receiving, at the cloud-based servers, a first donor geolocation of a donor computing device;
    transmitting a request for blood donation to the donor computing device based on the first donor geolocation;
    transmitting the recipient geolocation of the recipient computing device to the donor computing device;
    transmitting the first donor geolocation of the donor computing device to the recipient computing device;
    receiving, at the cloud-based servers, a second donor geolocation of the donor computing device;
    confirming the identity of the donor by a donor biometric identification process comprising at least one of:
        scanning an iris of the donor with the donor computing device to determine donor biometric iris information and identifying the donor based on the donor biometric iris information,
        scanning a face of the donor with the donor computing device to determine donor biometric facial information and identifying the donor based on the donor biometric facial information, or
        scanning a finger print of the donor with the donor computing device to determine donor biometric finger print information and identifying the donor based on the donor biometric finger print information;
    transmitting a confirmation of the identity of the donor to the recipient computing device;
    receiving a donation confirmation comprising information indicating a first volume of blood acquired from the donor, a first time when the first volume of blood was acquired, a second volume of blood delivered to the recipient, and a second time when the second volume of blood was delivered, wherein the first and second volumes of blood comprise the same blood, and further wherein the first volume of blood is equal to or greater than then second volume of blood;
    updating a donor record associated with the donor to comprise the information indicating the first volume of blood and the first time when the first volume of blood was acquired; and
    updating a recipient record associated with the recipient to comprise the information indicating the second volume of blood and the second time when the second volume of blood was delivered.

18. The biometric identification process as set forth in claim 17 wherein the recipient database and the donor database are the same database.

* * * * *